US009227002B1

(12) United States Patent
Giridharan et al.

(10) Patent No.: US 9,227,002 B1
(45) Date of Patent: Jan. 5, 2016

(54) SYSTEMS AND METHODS FOR PROVIDING CAVOPULMONARY SUPPORT

(71) Applicant: University of Louisville Research Foundation, Inc., Louisville, KY (US)

(72) Inventors: Guruprasad A. Giridharan, Louisville, KY (US); Steven C. Koenig, Louisville, KY (US); Michael A. Sobieski, Louisville, KY (US); Palaniappan Sethu, Louisville, KY (US); Mark D. Rodefeld, Indianapolis, IN (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/304,614

(22) Filed: Jun. 13, 2014

Related U.S. Application Data

(60) Provisional application No. 61/834,752, filed on Jun. 13, 2013.

(51) Int. Cl.
*A61N 1/362* (2006.01)
*A61M 1/12* (2006.01)

(52) U.S. Cl.
CPC ..................................... *A61M 1/122* (2014.02)

(58) Field of Classification Search
CPC ... A61M 1/1067; A61M 1/107; A61M 1/122; A61B 5/022; A61B 17/12
See application file for complete search history.

(56) References Cited

U.S. PATENT DOCUMENTS

2004/0147803 A1* 7/2004 Hegde et al. .................... 600/16

OTHER PUBLICATIONS

Rodefeld, et al., Cavopulmonary Assist: (Em)powering the Univentricular Fontan Circulation. Seminars in Thoracic and Cardiovascular Surgery: Pediatric Cardiac Surgery Annual, 2011;14(1):45-54.
Anderson, et al. Contemporary outcomes after the Fontan procedure: a Pediatric Heart Network multicenter study. J Am Coll Cardiol. 2008;52:85-98.
Hsu, et al., Heart Failure in Children. Part II: Diagnosis, Treatment, and Future Directions. Circ Heart Fail 2009; 2:490-8.
Goldberg, et al., Impact of oral sildenafil on exercise performance in children and young adults after the fontan operation: a randomized, double-blind, placebo-controlled, crossover trial. Circulation. 2011;123:1185-93.
Kanter, et al., Preliminary clinical experience with a bifurcated Y-graft Fontan procedure—a feasibility study. J Thorac Cardiovasc Surg. 2012;144:383-9.

(Continued)

*Primary Examiner* — Robert N Wieland
(74) *Attorney, Agent, or Firm* — Stites & Harbison, PLLC; Terry L. Wright

(57) ABSTRACT

Systems and methods for providing cavopulmonary support to a subject are provided that include and make use of a first inflatable extravascular cuff configured to be placed around a superior vena cava in the subject and a second inflatable extravascular cuff configured to be placed around an inferior vena cava in the subject. The system further includes a pump that is operably connected to both the first inflatable extravascular cuff and the second inflatable extravascular cuff, as well as a controller that is in communication with the pump. The controller receives one or more user-defined parameters and, in response to the user-defined parameters, independently controls the inflation and deflation of the first inflatable extravascular cuff and the second inflatable extravascular cuff to provide cavopulmonary support.

20 Claims, 8 Drawing Sheets

(56) References Cited

OTHER PUBLICATIONS

Mackling, et al. Management of single-ventricle patients with Berlin EXCOR ventricular assist device: Single-center experience. Artif Organs 2012; 36(6):555-9.
Vanderpluym, et al., The use of ventricular assist devices in pediatric patients with univentricular hearts. J Thorac Cardiovasc Surg 2011;141:588-90.
Newcomb, et al., Successful left ventricular assist device bridge to transplantation after failure of Fontan revision. J Heart Lung Transplant 2006;25:365-7.
Rodenfeld, et. al., Cavopulmonary assist: circulatory support for the univentricular Fontan circulation. Ann Thorac Surg 2003;76:1911-6.
Rodenfeld, et. al., Cavopulmonary assist for the univentricular Fontan circulation: von Karman viscous impeller pump. J Thorac Cardiovasc Surg 2010;140:529-36.
Giridharan, et al., Performance evaluation of a pediatric viscous impeller pump for Fontan cavopulmonary assist. Journal of Thoracic and Cardiovascular Surgery 2012; DOI: 10.1007/s13239-012-0096-4. (In press).
Kennington, et al., Design Optimization and Performance Studies of an Adult Scale Viscous Impeller Pump for Powered Fontan in an Idealized Total Cavopulmonary Connection. Cardiovascular Engineering and Technology 2011; 2(4):237-243.
Lacour-Gayet, et al., An artificial right ventricle for failing fontan: in vitro and computational study. Ann Thorac Surg. 2009;88(1):170-6.
Shiraishi, et al., Structural design of a newly developed pediatric circulatory assist device for Fontan circulation by using shape memory alloy fiber. Conf Proc IEEE Eng Med Biol Soc. 8353-5, 2011.
Drew, et al., Biomedical patient monitoring, data acquisition, and playback with LabVIEW®. In: Olansen JB, Rosow E, editors.Virtual bio-instrumentation: biomedical, clinical, and healthcare applications in LabVIEW®. Upper Saddle River, NJ: Prentice Hall; 2002; 92-98.
Koenig et al. Integrated data acquisition system for medical device testing and physiology research in compliance with Good Laboratory Practices. Biomed Instrum Technol 2004; 38:229-40.
Schroader, et al., Heart: an automated beat-to-beat cardiovascular analysis package using Matlab. Comput Biol Med 2004;34:371-88.
Giridharan, et al., A computer model of pediatric circulatory systems for testing pediatric assist devices. ASAIO J 2007; 53:74-81.
Pantalos, et al. Characterization of an adult mock circulation for testing cardiac support devices. ASAIO Journal, 2004; 50:37-46.
Giridharan, et al., Physiologic control of rotary blood pumps: An in vitro study. ASAIO Journal, 2004; 50:403-409.
Litwak, et al. Ascending aorta outflow graft location and pulsatile ventricular assist provide optimal hemodynamic support in an adult mock circulation. Artificial Organs, 2005; 29:629-635.
Kaebnick, et al., Quantification of pulsatility as a function of vascular input impedance: An in-vitro study. ASAIO Journal, 53(2):115-121, 2007.
Giridharan, et al., Cavopulmonary Assist for the Failing Fontan Circulation: Impact of Ventricular Function on Mechanical Support Strategy, ASAIO Journal, 2014, pp. 707-715.
Giridharan, et al., Performance evaluation of a pediatric viscous impeller pump for Fontan cavopulmonary assist, J Thorac Cardiovasc Surg. Jan. 2013; 145(1): 249-257.
Kerlo, et al., Experimental characterization of powered Fontan hemodynamics in an idealized total cavopulmonary connection model, Exp Fluids (2013) 54:1581.

\* cited by examiner

SYSTEMS AND METHODS FOR PROVIDING CAVOPULMONARY SUPPORT

RELATED APPLICATIONS

This application claims priority from U.S. Provisional Application Ser. No. 61/834,752, filed Jun. 13, 2013, the entire disclosure of which is incorporated herein by this reference.

TECHNICAL FIELD

The presently-disclosed subject matter relates to systems and methods for providing cavopulmonary support. In particular, the presently-disclosed subject matter relates to systems and methods for providing cavopulmonary support that make use of inflatable extravascular cuffs configured to be placed around the inferior and superior vena cava and provide cavopulmonary support to a subject.

BACKGROUND

Patients born with a single ventricle birth defect undergo a series of surgical procedures (three open heart surgeries) to directly connect the superior and inferior vena cava to the pulmonary arteries (Fontan), forming an approximately 'plus' shaped junction. In the plus shaped junction, the upper and lower vertical limbs are the superior and inferior vena cava and the horizontal limbs are the pulmonary arteries. In this regard, in a Fontan circulation, there is no right ventricle to power the pulmonary circulation. Both systemic and pulmonary circulations are powered by the single functional ventricle and, as such, these patients generally have a high risk of morbidity and mortality due to several factors including pulmonary hypertension, inability of the native single ventricle to support systemic and pulmonary circulations, and the need for a three-stage highly-invasive open heart surgical procedure.

Despite advances, palliative repair of functional single ventricle remains an enigmatic challenge. Late Fontan failure and attrition is becoming an increasingly problematic issue for which there is no primary therapy. Fontan failure is typically not the same as ventricular failure with systolic dysfunction. A majority (73%) of Fontan patients have normal systolic function and diastolic dysfunction. Indeed, the clinical manifestations of Fontan failure may be more a representation of decompensated systemic sequelae of Fontan physiology rather than that of primary ventricular failure.

Currently, the therapeutic options for failing Fontan patients are limited to medical therapy, surgical optimization, and mechanical circulatory support therapy. Medical therapy with diuretics, inotropes, and ACE-inhibitors provide some benefit, but only represent secondary therapy and do not fully restore long-term functional status. Surgical approaches to passively optimize total cavopulmonary connection (TCPC) to reduce power losses by 2-3 mmHg have been proposed. TCPC optimization may have tangible benefits but surgical modifications of the TCPC have yet to be applied clinically on a significant scale. Transplantation is a late surgical option, which has issues and concerns of its own, and does not currently represent an ideal long-term option. Patients with failing Fontan circulation have been implanted with a ventricular assist device (VAD) as a bridge to transplant. VADs unload the native ventricle, diminishing ventricular volume and external work, and augmenting the myocardial supply-demand ratio. While there have been reports of successful bridge to transplantation using VAD support in failing Fontan patients for brief periods of time, the results reported for post-cardiotomy bridge to transplantation have been poor. Additionally, pediatric bridge to transplant support of failing Fontan patients with a VAD is usually not successful.

A concerted effort is currently underway to develop cavopulmonary support devices (CSD) to power the Fontan circulation by delivering a modest pressure boost (approximately 5 mmHg) at the level of the total cavopulmonary connection (TCPC). In a univentricular Fontan circulation with preserved systolic function, CSD support will simultaneously decrease systemic venous pressure and increase ventricular preload. It would restore physiologic status to one more closely resembling more stable 2-ventricle physiology, in essence enabling clinical management of the patient as a "biventricular Fontan." Previous CSD designs include two catheter based microaxial pumps in the vena cava(e), or a single percutaneous pump that can augment Fontan flow in all 4 axes of the TCPC without risk of venous pathway obstruction. The catheter-based designs, however, while minimally invasive, can only be used for short-term support (2-4 weeks) due to the risk of septicemia. Further, percutaneous access would restrict the mobility of the patients implanted with these devices. Right ventricular assist devices have been implanted for chronic support in failing Fontan patients but it requires take down of the TCPC and have limited long-term success. Further, all the CSD designs to date are blood contacting and have significant risk of thrombosis, requiring anticoagulation therapy.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes systems and methods for providing cavopulmonary support. In particular, the presently-disclosed subject matter includes systems and methods for providing cavopulmonary support that make use of inflatable extravascular cuffs configured to be placed around the inferior and superior vena cava and provide cavopulmonary support to a subject.

In one exemplary embodiment of the presently-disclosed subject matter, a system for providing cavopulmonary support to a subject is provided that includes a first inflatable extravascular cuff that is configured to be placed around a superior vena cava in a subject, and a second inflatable extravascular cuff that is configured to be placed around an inferior vena cava in a subject. A pump is operably connected to both the first inflatable extravascular cuff and the second inflatable extravascular cuff, and communicates with both the first inflatable extravascular cuff and the second inflatable extravascular cuff through a number of fluid supply lines that are attached to the first inflatable extravascular cuff and the second inflatable extravascular cuff. In this regard, by making use of multiple fluid supply lines, the first inflatable extravascular cuff and the second inflatable extravascular cuff can be inflated or deflated independently from one another.

The system further includes a controller that communicates with the pump and receives one or more user-defined parameters that are directed to a selected timing for inflating and deflating the first inflatable extravascular cuff, the second inflatable extravascular cuff, or both. As the user-defined parameters are inputted into and received by the controller, the pump then subsequently delivers or retracts metered pulses of fluid, i.e., pneumatic or hydraulic, through the fluid supply lines to independently inflate or deflate the first inflatable extravascular cuff and the second inflatable extravascular cuff.

To further provide control over the inflation and deflation of the first inflatable extravascular cuff and the second inflatable extravascular cuff, in some embodiments, an exemplary system for providing cavopulmonary support can also include a pressure sensor and a flow sensor for directly measuring fluid flow (device stroke volume) and driveline pressure of the system. In such embodiments, upon measuring the pressure and flow of blood in the subject, the pressure sensor and the flow sensor can operate to communicate data relating to the pressure and device stroke volume to the controller and, in response to that pressure and flow data, the controller can output a control signal to the pump to alter the timing of the inflation and deflation of the first inflatable extravascular cuff, the second inflatable extravascular cuff, or both to thereby alter the level of cavopulmonary support being provided to the subject.

With respect to the first inflatable extravascular cuff and the second inflatable extravascular cuff included in a system of the presently-disclosed subject matter, the first inflatable extravascular cuff and the second inflatable extravascular cuff can be provided in various configurations and can include a number of different features to affect the inflation and deflation of the extravascular cuffs and to affect the cavopulmonary support provided by the present systems. For example, in some embodiments, the first inflatable extravascular cuff and the second inflatable extravascular cuff can each include a proximal chamber and a distal chamber, which are separated from one another and are independently connected to one of the fluid supply lines. In this regard, in some embodiments, each proximal chamber can be controlled and inflated and/or deflated independently from each distal chamber to provide cavopulmonary support. For example, in some embodiments that make use of inflatable extravascular cuffs having a proximal chamber and a distal chamber, the first inflatable extravascular cuff can be placed around the superior vena cava and the second inflatable extravascular cuff can then be placed around the inferior vena cava. Upon placement of the first inflatable extravascular cuff and the second inflatable extravascular cuff, each of the distal chambers are inflated first. The proximal chambers of the first inflatable extravascular cuff and the second inflatable extravascular cuff are then each subsequently inflated while the distal chambers remain inflated. To minimize retrograde flow, the distal chambers of the first inflatable extravascular cuff and the second inflatable extravascular cuff are then deflated while the proximal chambers remain inflated for a period of time before deflating. In some embodiments, the peristaltic action provided by such a sequential inflation and deflation of the proximal and distal chambers maximizes device efficiency and forward flow of blood to the pulmonary arteries, while minimizing the total stroke volume and retrograde flow observed with the system. In some embodiments, to further maximize the flow achieved as a result of the inflation and deflation of the distal chambers and the proximal chambers of the first inflatable extravascular cuff and the second inflatable extravascular, the user-defined parameters received by the controller of an exemplary system can include a time delay between the inflation or the deflation of the distal chambers and the proximal chambers of the first inflatable extravascular cuff and the second inflatable extravascular.

With further respect to the extravascular cuffs used in accordance with the presently-disclosed subject matter, in other embodiments, inflatable extravascular cuffs are provided for use in an exemplary system that each have length sufficient to allow the inflatable extravascular cuffs to be spirally wound around the superior vena cava or the inferior vena cava of a subject. In another embodiment, an extravascular cuff provided for use in an exemplary system can be characterized as including an upper end, a central portion, and a lower end that collectively define a hollow chamber of the extravascular cuff. Within the hollow chamber, such an extravascular cuff further includes a plurality of internal barriers that are spaced apart from one another and that define a serpentine path through the hollow chamber. A fluid supply line for inflating and deflating the extravascular cuff is further included at the lower end or in the central portion of the extravascular cuff and is in fluid communication with the hollow chamber. As such, when the extravascular cuff is placed around a blood vessel and is inflated, the positioning of the fluid supply line as well as the internal barriers allow the extravascular cuff to inflate in a peristaltic-like manner from a particular area of the extravascular cuff.

In further embodiments of the presently-disclosed subject matter, one or more of the extravascular cuffs can also be placed around the left pulmonary artery, the right pulmonary artery, or both of a subject to provide an additional level of cavopulmonary support. For instance, in some embodiments, a system can be provided that includes a first inflatable extravascular cuff configured to be placed around the superior vena cava, a second inflatable extravascular cuff configured to be placed around the inferior vena cava, a third inflatable extravascular cuff configured to be placed around the left pulmonary artery, and a fourth inflatable extravascular cuff configured to be placed around the right pulmonary artery. Each of the extravascular cuffs can then be operably connected to a pump in communication with a controller that will independently control the inflation and deflation of each cuff.

Still further provided by the presently-disclosed subject matter are methods for providing cavopulmonary support to a subject that make use of the systems described herein. In some embodiments, a method for providing cavopulmonary support to a subject includes a step of initially providing a system that includes a first inflatable extravascular cuff configured to be placed around a superior vena cava in the subject and a second inflatable extravascular cuff configured to be placed around an inferior vena cava in a subject. The first inflatable extravascular cuff and/or the second inflatable extravascular cuff can then be selectively inflated to provide an amount of cavopulmonary support. In some implementations of the methods, the system further comprises a controller for receiving one or more user-defined parameters and for independently controlling the inflation and deflation of the first inflatable extravascular cuff and the second inflatable extravascular cuff in response to the user-defined parameters. As described above, such user-defined parameters can be inputted directly into the controller and can be directed to a selected timing for inflating and deflating the first inflatable extravascular cuff, the second inflatable extravascular cuff, or both to provide cavopulmonary support. In certain implementations, the user-defined parameters can be inputted in a manner that causes the first inflatable extravascular cuff and the second inflatable extravascular cuff to inflate and deflate to alter one or more conditions selected from the group consisting of cavopulmonary pressure head, cardiac output, pulmonary artery pressure, aortic systolic pressure, aortic diastolic pressure, left ventricular end-systolic volume, left ventricular end-diastolic volume, and combinations thereof.

Further features and advantages of the present invention will become evident to those of ordinary skill in the art after a study of the description, figures, and non-limiting examples in this document.

DESCRIPTION OF EXEMPLARY EMBODIMENTS

Figure 1:
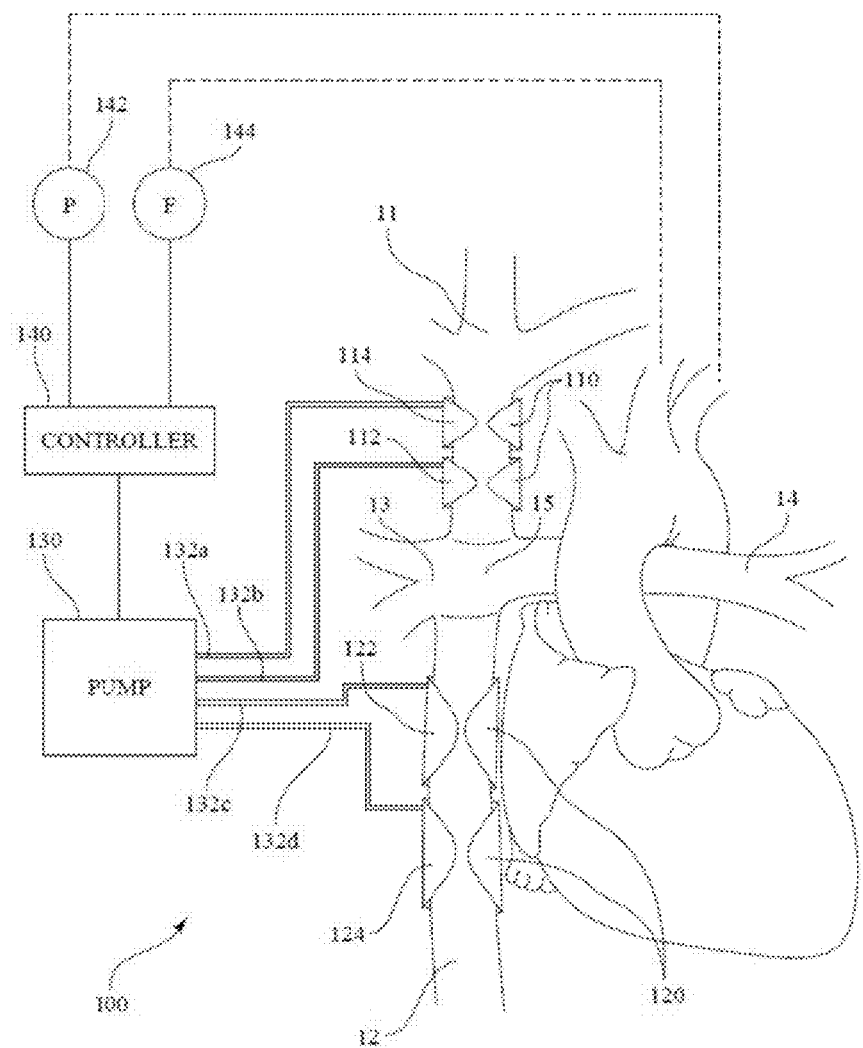
FIG. 1 is a schematic diagram showing the placement of an exemplary cavopulmonary support system made in accordance with the presently-disclosed subject matter.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "processing device" is used herein to describe one or more microprocessors, microcontrollers, central processing units, Digital Signal Processors (DSPs), Field-Programmable Gate Arrays (FPGAs), Application-Specific Integrated Circuits (ASICs), or the like for executing instructions stored on a data storage device.

The term "data storage device" is understood to mean physical devices (computer readable media) used to store programs (sequences of instructions) or data (e.g. program state information) on a non-transient basis for use in a computer or other digital electronic device, including primary memory used for the information in physical systems which are fast (i.e. RAM), and secondary memory, which are physical devices for program and data storage which are slow to access but offer higher memory capacity. Traditional secondary memory includes tape, magnetic disks and optical discs (CD-ROM and DVD-ROM). The term "memory" is often (but not always) associated with addressable semiconductor memory, i.e. integrated circuits consisting of silicon-based transistors, used for example as primary memory but also other purposes in computers and other digital electronic devices. Semiconductor memory includes both volatile and non-volatile memory. Examples of non-volatile memory include flash memory (sometimes used as secondary, sometimes primary computer memory) and ROM/PROM/EPROM/EEPROM memory. Examples of volatile memory include dynamic RAM memory, DRAM, and static RAM memory, SRAM.

The presently-disclosed subject matter includes systems and methods for providing cavopulmonary support. In particular, the presently-disclosed subject matter includes systems and methods for providing cavopulmonary support that make use of inflatable extravascular cuffs configured to be placed around the inferior and superior vena cava and provide cavopulmonary support to a subject.

Referring first to FIG. 1, in one exemplary embodiment of the presently-disclosed subject matter, a system 100 for providing cavopulmonary support to a subject is provided that includes a first inflatable extravascular cuff 110 that is configured to be placed around a superior vena cava 11 in a subject, and a second inflatable extravascular cuff 120 that is configured to be placed around an inferior vena cava 12 in a subject. A pump 130 is operably connected to both the first inflatable extravascular cuff 110 and the second inflatable extravascular cuff 120, and communicates with both the first inflatable extravascular cuff 110 and the second inflatable extravascular cuff 120 through a number fluid supply lines 132a, 132b, 132c, 132d that are attached to the first inflatable extravascular cuff 110 and the second inflatable extravascular cuff 120. In this regard, by making use of multiple fluid supply lines 132a, 132b, 132c, 132d, the first inflatable extravascular cuff 110 and the second inflatable extravascular cuff 120, including particular portions of the first inflatable extravascular cuff 110 and the second inflatable extravascular cuff 120, can be inflated or deflated independently from one another to provide cavopulmonary support, as described in further detail below.

The system 100 further includes a controller 140 that communicates with the pump 130 and receives one or more user-defined parameters that are from a user input and that are directed to a selected timing for inflating and deflating the first inflatable extravascular cuff 110, the second inflatable extravascular cuff 120, or both. As the user-defined parameters are inputted into and received by the controller 140, the user-defined parameters are stored in a data storage device (not shown) associated with the controller 140. Then, based on the received user-defined parameters, a processing device (also not shown), which is further associated with the controller 140, outputs a control signal to the pump 130. The pump 130 then subsequently delivers or retracts metered pulses of fluid, i.e., pneumatic or hydraulic, through the fluid supply lines 132a, 132b, 132c, 132d to independently inflate or deflate the first inflatable extravascular cuff 110 and the second inflatable extravascular cuff 120.

To further provide control over the inflation and deflation of the first inflatable extravascular cuff 110 and the second inflatable extravascular cuff 120, the exemplary system 100 for providing cavopulmonary support can also include a pressure sensor 142 and a flow sensor 144 for directly measuring the fluid flow (device stroke volume) and driveline pressure of the system and/or the actual pressure and flow of the blood in the subject. Numerous sensors can, of course, be used to directly measure such pressure and flow and can be placed in communication with various blood vessels of the subject (e.g., the aorta) or can be placed within the first inflatable extravascular cuff 110 and/or the second inflatable extravascular cuff 120 themselves. Irrespective of the type and placement of the pressure sensor 142 and the flow sensor 144, however, upon measuring the pressure and flow of blood in the subject, the pressure sensor 142 and the flow sensor 144 can then operate to communicate data relating to the pressure and flow of blood in the subject to the controller 140. In response to that pressure and flow data, the controller 140 can then output a control signal to the pump 130 to alter the timing of the inflation and deflation of the first inflatable extravascular cuff 110, the second inflatable extravascular cuff 120, or both to thereby alter the level of cavopulmonary support being provided to the subject, as described below.

Turning now to the first inflatable extravascular cuff 110 and the second inflatable extravascular cuff 120 included in the system 100, the first inflatable extravascular cuff 110 and the second inflatable extravascular cuff 120 can generally be made from a number of materials that are sufficiently flexible and biocompatible, and that can safely be implanted in a subject and placed around the blood vessels in the subject's body without causing damage. The extravascular cuffs used in accordance with the systems and methods of the presently-disclosed subject matter can also be provided in various configurations and can include a number of different features that affect the inflation and deflation of the extravascular cuffs and that affect the cavopulmonary support provided by the systems of the presently-disclosed subject matter. For example, and referring still to FIG. 1, in the system 100, the first inflatable extravascular cuff 110 includes a proximal chamber 112 and a distal chamber 114, and the second inflatable extravascular cuff 120 also includes a proximal chamber 122 and a distal chamber 124. The proximal chamber 112 and the distal chamber 114 of the first inflatable extravascular cuff 110 as well as the proximal chamber 122 and the distal chamber 124 of the second inflatable extravascular cuff 120 are each separated from one another and are each independently connected to one of the fluid supply lines 132a, 132b, 132c, 132d. As such, in the system 100, each proximal chamber 112, 122 can be controlled and inflated and/or deflated independently from each distal chamber 114, 124 to provide cavopulmonary support.

For example, in some embodiments, and referring now to FIGS. 1 and 5A-5D, the system 100 can be operated in the following manner. In a subject that includes a total cavopulmonary connection (i.e., where the superior vena cava 11 and the inferior vena cava 12 are directly connected to the left pulmonary artery 14 and the right pulmonary artery 13, and form an approximately 'plus' shaped junction 15), the first inflatable extravascular cuff 110 can first be placed around the superior vena cava 11, with the proximal chamber 112 of the first inflatable extravascular cuff 110 positioned closest to the junction 15 and the distal chamber 114 of the first inflatable extravascular cuff 110 positioned further away from junction 15. The second inflatable extravascular cuff 120 can then be placed around the inferior vena cava 12, with the proximal chamber 122 of the second inflatable extravascular cuff 120 positioned closest to the junction 15 and the distal chamber 124 of the second inflatable extravascular cuff 120 positioned further away from junction 15.

Figure 5A:
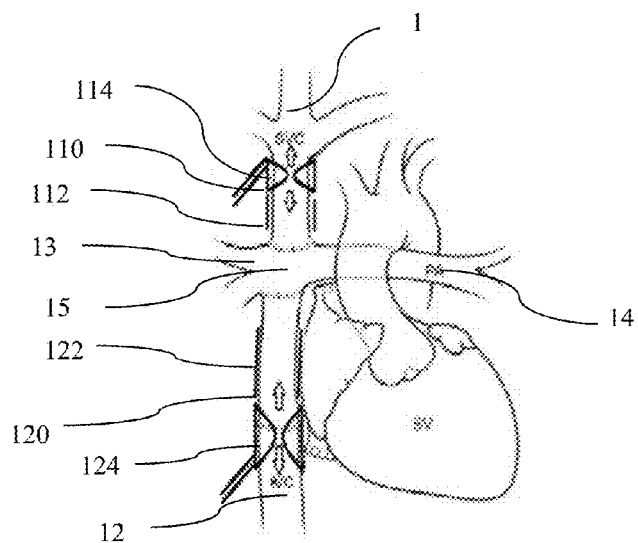
FIGS. 5A-5D are a series of schematic diagrams showing the placement and the inflation and deflation of exemplary inflatable extravascular cuffs around the superior and inferior vena cava of a subject.
Figure 5B:
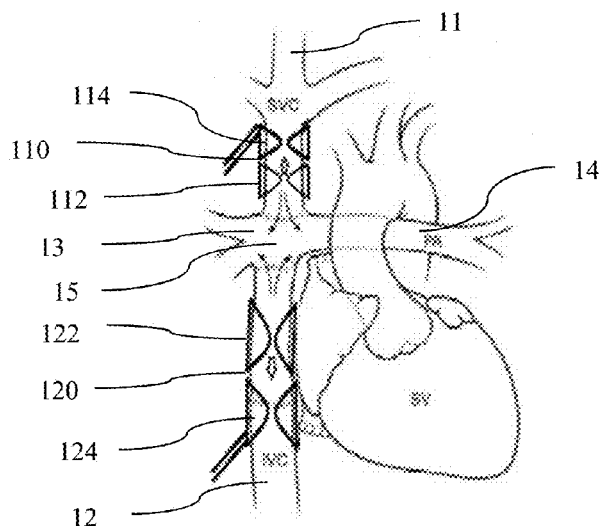
Figure 5C:
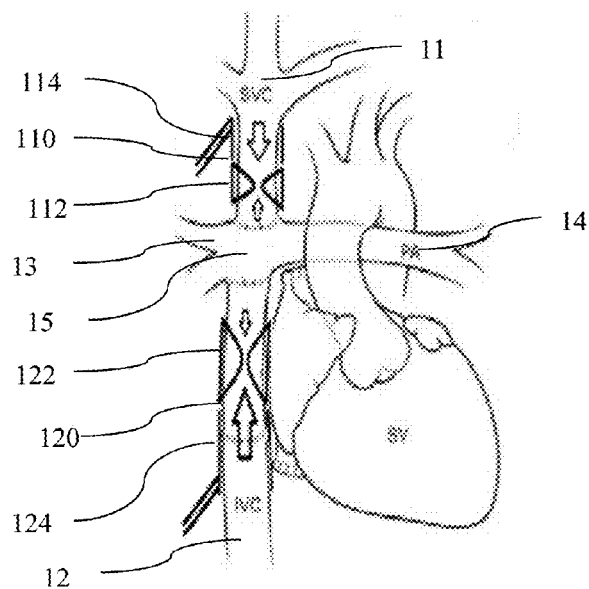
Figure 5D:
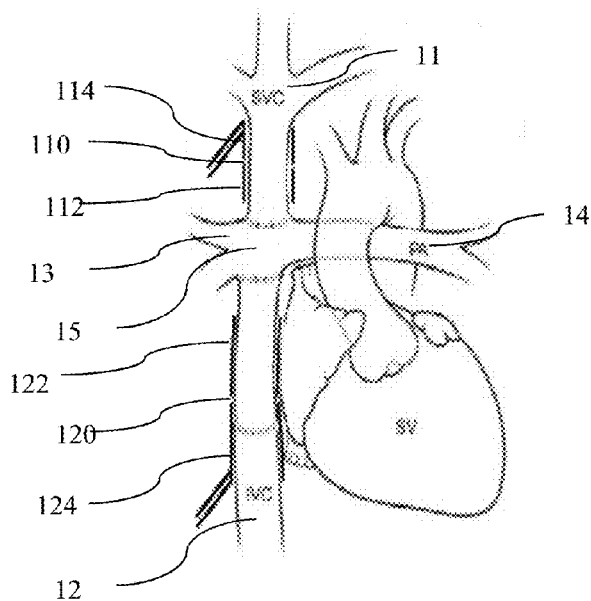

Upon placement of the first inflatable extravascular cuff 110 and the second inflatable extravascular cuff 120, to provide cavopulmonary support, each of the distal chambers 114, 124 are inflated first such that that half of the displacement volume achieved by the first inflatable extravascular cuff 110 and the second inflatable extravascular cuff 120 is pushed towards the pulmonary arteries 13 and 14, as shown in FIG. 5A. The proximal chambers 112, 122 of each of the inflatable extravascular cuffs 110, 120 are subsequently inflated while the distal chambers 114, 124 remain inflated to ensure that the remainder and the majority of the displacement volume reaches the pulmonary arteries 13, 14, as shown in FIG. 5B. To minimize retrograde flow through the junction 15 and into the superior vena cava 11 and inferior vena cava 12, the distal chambers 114, 124 of the first inflatable extravascular cuff 110 and the second inflatable extravascular 120 are then deflated while the proximal chambers 112, 122 remain inflated for a period of time before deflating, as shown in FIGS. 5C-5D. It is, of course, contemplated that this sequential inflation and deflation of the distal chambers 114, 124 and the proximal chambers 112, 122 of the first inflatable extravascular cuff 110 and the second inflatable extravascular 120, including the timing and the rate (e.g., beats per minute) of inflation, can be tailored to provide a suitable level of cavopulmonary support for a particular subject. Without wishing to be bound by any particular theory or mechanism, however, it is believed that the peristaltic action provided by the sequential inflation and deflation maximizes device efficiency and forward flow of blood to the pulmonary arteries 13, 14 while minimizing the total stroke volume and retrograde flow observed with the system 100.

In certain embodiments, to further maximize the flow achieved as a result of the inflation and deflation of the distal chambers 114, 124 and the proximal chambers 112, 122 of the first inflatable extravascular cuff 110 and the second inflatable extravascular 120, the user-defined parameters received by the controller 140 of the system 100 can include a time delay between the inflation and the deflation of the distal chambers 114, 124 and the proximal chambers 112, 122 of the first inflatable extravascular cuff 110 and the second inflatable extravascular cuff 120. For instance, in some embodiments, it has been observed that for a given inflation/deflation rate (e.g., 80 beats per minute), a time delay of about 150 to about 175 milliseconds between the inflation and the deflation the distal chambers 114, 124 and the proximal chambers 112, 122 in both the first inflatable extravascular cuff 110 and the second inflatable extravascular 120 can serve to increase the flow of blood to the pulmonary arteries provided by the system 100. In some embodiments, the stroke volume achieved by inflating the first inflatable extravascular cuff 110 and the second inflatable extravascular cuff 120 can be augmented by increasing the inflation pressure of the cuffs and/or by controlling the fluid flow into the cuff.

As a refinement of the extravascular cuffs used in accordance with the presently-disclosed subject matter, the first inflatable extravascular cuff 110 and the second inflatable extravascular cuff 120 described herein above are each provided with entirely separate proximal and distal chambers, as shown in FIGS. 1 and 5A-5D. It is further contemplated, however, that an extravascular cuff including a proximal and a distal chamber can be provide as a unitary construction in which the proximal chamber and distal chamber of each cuff are connected directly to one another and are separated by a barrier. In some embodiments, such an extravascular cuff can be provided where the barrier between the proximal and distal chamber defines a small opening between the proximal and distal chamber, and can be used as a built-in time delay when inflating such an extravascular cuff from either the proximal or distal chamber. For example, in such embodiments, it has been observed that about a 0.07 inch to about a 0.1 inch opening between the proximal and distal chambers can provide a time delay between the inflation of the proximal chamber and the distal chamber of between 100 and 175 ms.

Figure 2:
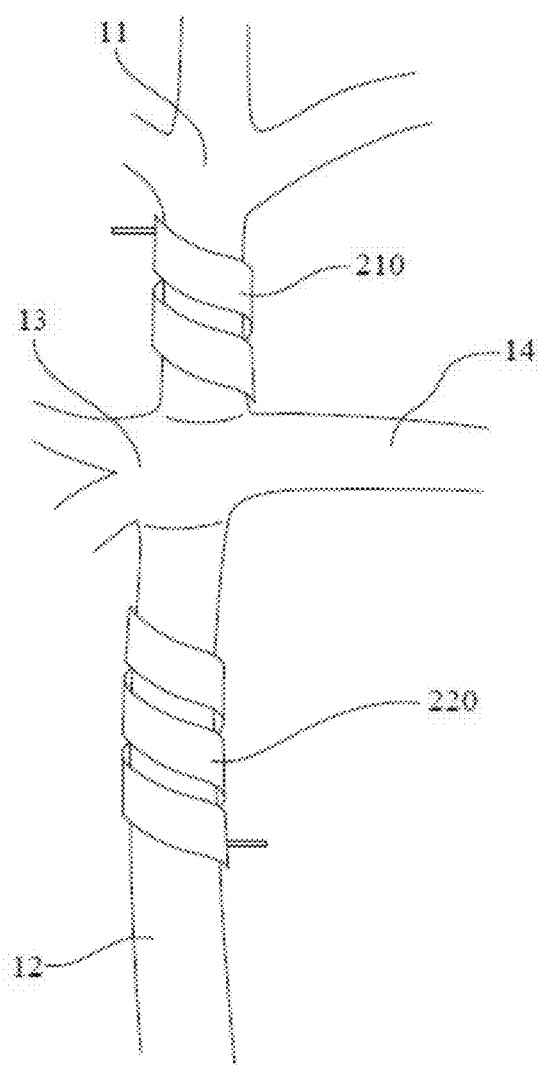
FIG. 2 is a schematic diagram showing placement of an exemplary inflatable extravascular cuff made in accordance with presently-disclosed subject matter.

As another refinement to the extravascular cuffs used in accordance with the presently-disclosed subject matter, and referring now to FIG. 2, in some embodiments, inflatable extravascular cuffs 210, 220 are provided for use in an exemplary system that each have length sufficient to allow the inflatable extravascular cuffs 210, 220 to be spirally wound around the superior vena cava 11 or the inferior vena cava 12, respectively, of a subject. In this regard, in such embodiments, the inflatable extravascular cuffs can be inflated initially from a position distal to the pulmonary arteries 13, 14 to a position adjacent to the pulmonary arteries 13, 14 to thereby provide for a forward flow of blood from the superior vena cava 11 or the inferior vena cava 12 and into the pulmonary arteries 13, 14. Similarly, the spirally wound extravascular cuffs 210, 220 can also be deflated in the same manner (i.e., from a position distal to the pulmonary arteries 13, 14 to a position adjacent to the pulmonary arteries 13, 14) to thereby prevent retrograde flow into the superior vena cava 11 or the inferior vena cava 12 from the pulmonary arteries 13, 14.

Figure 3:
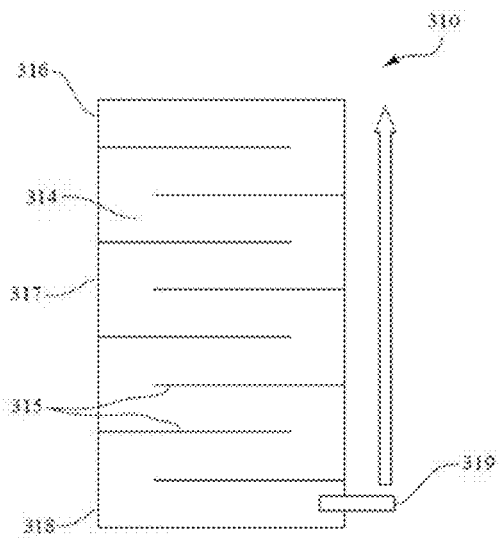
FIG. 3 is a schematic diagram showing another exemplary inflatable extravascular cuff made in accordance with the presently-disclosed subject matter.

As yet another refinement to the extravascular cuffs used in accordance with the presently-disclosed subject matter, and referring now to FIG. 3, in another embodiment, an extravascular cuff 310 is provided for use in an exemplary system that has a width sufficient to allow the extravascular cuff 310 to be wrapped around a blood vessel and can be characterized as including an upper end 316, a central portion 317, and a lower end 318 that collectively define a hollow chamber 314. Within the hollow chamber 314, the extravascular cuff 310 further includes a plurality of internal barriers 315 that are spaced apart from one another and define a serpentine path through the hollow chamber 314. A fluid supply line 319 for inflating and deflating the extravascular cuff 310 is further included at the lower end 318 of the extravascular cuff 310 and is in fluid communication with the hollow chamber 314. In this regard, when the extravascular cuff 310 is placed around a blood vessel and is inflated, the positioning of the fluid supply line 319 at the lower end 318 of the extravascular cuff 310 as well as the internal barriers 315 allow the extravascular cuff 310 to inflate in a peristaltic-like manner from the lower end 318 to the upper end 316, and thereby allow for a forward flow of blood within a blood vessel regardless of effects of gravity.

Figure 4:
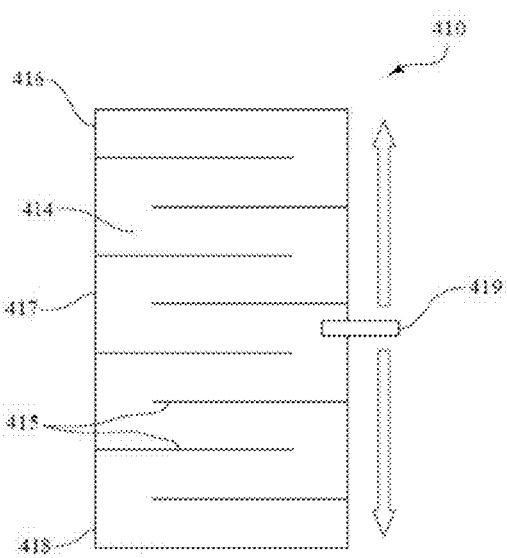
FIG. 4 is a schematic diagram showing another exemplary inflatable extravascular cuff made in accordance with the presently-disclosed subject matter.

As an alternative to the extravascular cuff 310 shown in FIG. 3, in some embodiments and referring now to FIG. 4, an extravascular cuff 410 is provided that also includes an upper end 416, a central portion 417, a lower end 418, a hollow chamber 414, a plurality of internal barriers 415, and a fluid supply line 419. However, unlike the extravascular cuff 310 shown in FIG. 3, the fluid supply line 419 of the extravascular cuff 410 is not positioned at the lower end 418 of the extravascular cuff 410. Rather, in the extravascular cuff 410, the fluid supply line 419 is positioned in the central portion 417 such that, upon introducing an amount of fluid through the fluid supply line 419, the extravascular cuff 410 inflates in a bidirectional manner from the central portion 417 toward both the upper end 416 and the lower end 418 of the extravascular cuff 410. In some embodiments, such a bidirectional inflation of the extravascular cuff 410 can be useful for wrapping around blood vessels such as the aortic arch to prevent coronary steal.

Any of the inflatable extravascular cuffs 110, 120, 210, 220, 310, 410 described herein above with reference to FIGS. 1-4 can be placed around the superior and inferior vena cava of a subject and used to provide cavopulmonary support to the subject, or can be placed around other blood vessels (e.g., the aorta) such that the systems are more broadly applied to the systemic circulation and provide cardiac support. In some embodiments, the cuffs 110, 120, 210, 220, 310, 410 can be directly sutured to or around the blood vessels themselves or can be sutured to or incorporated into a suitable graft. In other embodiments, and although not shown in FIGS. 1-4, the cuffs 110, 120, 210, 220, 310, 410 can be placed around collapsible cannulas that are incorporated into the cavopulmonary junction of a particular subject. For example, in some embodiments, an artificial cavopulmonary junction that includes four collapsible cannulas in fluid communication with one another can be utilized to form the "plus" of the cavopulmonary junction and one of the extravascular cuffs 110, 120, 210, 220, 310, 410 can be placed around each of the collapsible cannulas or can be incorporated directly into the artificial cavopulmonary junction to provide a prefabricated junction including both cannulas for attachment to the blood vessels of a subject and cuffs for directly controlling the flow of blood through the junction.

In still further embodiments of the presently-disclosed subject matter, one or more of the extravascular cuffs 110, 120, 210, 220, 310, 410 can also be wrapped around the left pulmonary artery, the right pulmonary artery, or both of a subject to provide an additional level of cavopulmonary support. For instance, in some embodiments, a system can be provided that includes a first inflatable extravascular cuff configured to be placed around the superior vena cava, a second inflatable extravascular cuff configured to be placed around the inferior vena cava, a third inflatable extravascular cuff configured to be placed around the left pulmonary artery, and a fourth inflatable extravascular cuff configured to be placed around the right pulmonary artery. Each of the extravascular cuffs can then be operably connected to a pump in communication with a controller that will independently control the inflation and deflation of each cuff. Of course, the cuffs placed around the vena cavae and the pulmonary arteries (or artificial cavopulmonary connection cannulae that connect to these vessels) can be inflated simultaneously or in a specific sequence to assist pulmonary circulation and provide cavopulmonary support. In some embodiments, however, because the vena cavae and pulmonary arteries have no valves within them and because implanting artificial valves can be problematic as valves in the pulmonary circulation have been known to induce thrombus formation, the first and second extravascular cuffs placed around the superior and inferior vena cavae will inflate first to improve the efficacy of the system. Then, while the first and second extravascular cuffs placed around the superior and inferior vena cavae are inflated, the third and fourth extravascular cuffs placed around the right and left pulmonary artery, respectively, can subsequently be inflated to minimize retrograde flow through the vena cavae. After inflation of each of the extravascular cuffs, the first and second extravascular cuffs placed around the superior and inferior vena cavae can then be deflated first while the third and fourth extravascular cuffs placed around the right and left pulmonary artery remain inflated to prevent retrograde flow through the pulmonary arteries. Upon the deflation of the first and second extravascular cuffs, the third and fourth extravascular cuffs can then be deflated and the process repeated to provide cavopulmonary support.

Still further provided by the presently-disclosed subject matter are methods for providing cavopulmonary support to a subject that make use of the systems described herein. In some embodiments, a method for providing cavopulmonary support to a subject includes initially providing a system including a first inflatable extravascular cuff configured to be placed around a superior vena cava in the subject and a second inflatable extravascular cuff configured to be placed around an inferior vena cava in a subject. The first inflatable extravascular cuff and/or the second inflatable extravascular cuff can then be selectively inflated to provide an amount of cavopulmonary support. In some implementations of the methods, the system further comprises a controller for receiving one or more user-defined parameters and for independently controlling the inflation and deflation of the first inflatable extravascular cuff and the second inflatable extravascular cuff in response to the user-defined parameters. As described above, such user-defined parameters can be inputted directly into the controller and can be directed to a selected timing for inflating and deflating the first inflatable extravascular cuff, the second inflatable extravascular cuff, or both to provide cavopulmonary support. In certain implementations, the user-defined parameters can be inputted in a manner that causes the first inflatable extravascular cuff and the second inflatable extravascular cuff to inflate and deflate to alter one or more conditions selected from the group consisting of cavopulmonary pressure head, cardiac output, pulmonary artery pressure, aortic systolic pressure, aortic diastolic pressure, left ventricular end-systolic volume, left ventricular end-diastolic volume, and combinations thereof.

The above-described methods and systems, which make use of inflatable extravascular cuffs for providing cavopulmonary support are important as an alternative to traditional support devices as the systems and method of the presently-disclosed subject matter are capable of providing cavopulmonary support to a subject in a manner that advantageously allows for: (1) a lack of contact with blood; (2) the ability to stop the device for a prolonged period and enable weaning of the device support if warranted; (3) the ability to not block flow after implantation; (4) the ability to avoid air embolisms in the event of a rupture of the cuffs; (5) the ability to implant the cuffs (and the artificial cavopulmonary junction) in a single open heart surgery or a minimally invasive surgical procedure, which may allow for reduction in the number of surgeries needed for Fontan conversion (currently three surgeries—Norwood, Glenn & Fontan procedures); (6) the ability to allow the patient to move and be ambulatory when catheter-based devices require the patient to be bed-ridden; (7) the ability to use materials that have already been implanted in humans and to use readily-available pneumatic and electrohydraulic drivers; (8) the ability to support a patient for years and not weeks; (9) the ability to use a device that need not be synchronized to heart rate like IABPs or counterpulsation devices; (10) the ability to increase flow by increasing the frequency of the device inflation and deflation cycles and to reduce the number of cycles to reduce support to assess patient condition and to assist weaning; (11) the ability to control the cuff lengths, inflation pressures, and volumes to cater to individual patient's anatomy (e.g.,) the cuff on the inferior vena cava may be longer and displace a larger volume compared to the cuff on the superior vena cava; (12) the ability to use cuffs that need not be of equal dimensions and the ability to reduce the number of cuffs if anatomy prevents it; (13) the ability to use a system where vena cavae offsets or pulmonary artery offsets (improper 'plus' junction) will not affect device performance significantly; (14) the ability to restore pulmonary pressure pulsatility which may reduce pulmonary hypertension further improving patient status; and (15) the ability to also use nozzle diffusers to passively promote forward flow in a subject.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals that are kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter is further illustrated by the following specific but non-limiting examples.

EXAMPLES

Materials and Methods for Examples 1-2

Peristaltic Cavopulmonary Support System ("CPAD"):

The CPAD consists of a pneumatically driven, dual-chambered, non-blood contacting extra-vascular cuffs that can be placed around the vena cavae or vena caval grafts. The CPAD may be sequentially driven by a portable pneumatic driver that weighs approximately 2 kg. The CPAD chamber distal to the TCPC is inflated first with approximately half of this CPAD chamber's displacement volume going towards the pulmonary arteries (FIG. 5A). The proximal CPAD chamber is subsequently inflated while the distal CPAD chamber is fully inflated (FIG. 5B). This inflation sequence ensures that the majority of the displacement volume of the proximal chamber is directed towards the pulmonary arteries. To minimize retrograde flow through the TCPC, the distal CPAD chamber is deflated first with the proximal chamber inflated (FIG. 5C), and the proximal chamber is subsequently deflated (FIG. 5D). This peristaltic action maximizes system efficiency and forward flow to pulmonary arteries while minimizing total CPAD stroke volume and retrograde flow.

Figure 6A:
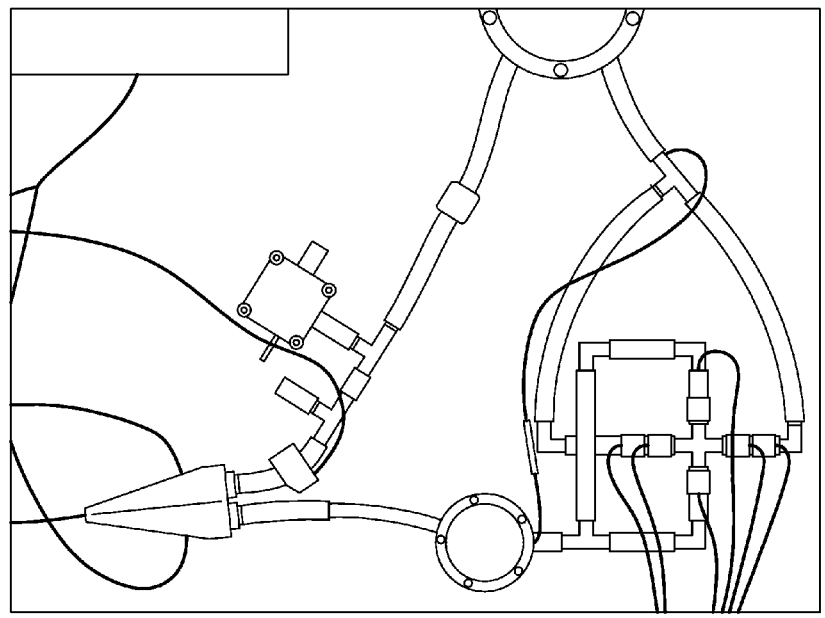
FIGS. 6A-6B include images showing: a pediatric Fontan mock circulatory system including a single ventricle, an aorta, arterial compliance, systemic vascular resistance, venous compliance, a Fontan junction connected to four extravascular cuffs, pulmonary resistance, and pulmonary compliance elements (FIG. 6A); and a 2-kg portable pneumatic driver that was used to drive the system (FIG. 6B)
Figure 6B:
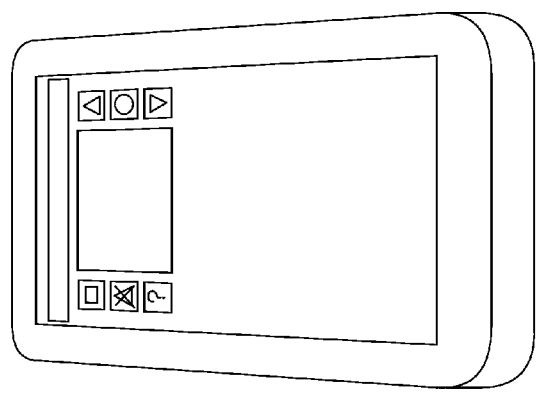

Mock Circulation Study:

Mock circulation systems consisting of a silicone ventricle, aorta, systemic and pulmonic resistances and compliances, and a cavopulmonary junction with significant vena caval offset were used to simulate adult and pediatric univentricular Fontan circulations (FIG. 6A). A rigid four-way junction with vena caval offset connected to compliant 19 mm outer diameter thin walled latex tubing (Penrose drain) was used to simulate vena cavae and pulmonary arteries of the adult TCPC. Pediatric TCPC was simulated using 12.7 mm outer diameter thin walled latex tubing for vena cavae and pulmonary arteries. Ventricular pressure, heart rate, systemic and pulmonary resistances and compliances were adjusted to reproduce hemodynamic waveforms of univentricular Fontan physiology of adults. Baseline hemodynamic pressure and flow data were collected for the univentricular Fontan circulation (no CPAD support). Prototype peristaltic devices fabricated from neonatal blood pressure cuffs were placed on the superior and inferior vena cavae and pulmonary arteries. The CPAD was driven by a pneumatic driver (Thoratec, Pleasanton, Calif.) or a 2-kg portable pneumatic driver (SCR Inc., Louisville, Ky.) (FIG. 6B). The CPAD was operated at different configurations (SVC only, IVC only, SVC and IVC), stroke volumes (8-48 mL), CPAD beat rates (30-120 bpm), and time delays between CPAD chambers (0-250 ms in 25 ms intervals) with the mock ventricle turned off (static testing) to optimize CSD design and timing. Additionally, the peristaltic CPAD was operated at different configurations (SVC only, IVC only, SVC and IVC, vena cavae, and pulmonary arteries), stroke volumes (8-48 mL), CPAD beat rates (30-120 bpm), and time delays between CPAD chambers (0-250 ms in 25 ms intervals) with the mock circulatory system simulating Fontan circulation (dynamic testing) to test the efficacy of the peristaltic CPAD to support failing Fontan circulation. The potential of the CPAD to impede Fontan cavopulmonary flow during pump failure was studied by stopping CPAD with the device in place. The performance of the CPAD was compared to (1) a rotary cavopulmonary assist device (Viscous Impeller Pump, Indianapolis, Ind.) and, (2) a single chambered cuff implanted on the IVC (non-peristaltic).

Data Collection and Analysis:

Hemodynamic data were collected using a clinically approved GLP—compliant data acquisition system. All transducers were pre- and post-calibrated against known standards to ensure measurement accuracy. Pressure and flow waveforms were used to calculate heart rate, stroke volume, cardiac output, mean aortic pressure (AoP), cavopulmonary pressures, left atrial pressure, and aortic and cavopulmonary flows on a beat-to-beat basis by using the HEART program developed in Matlab (MathWorks, Natick, Mass.) and averaged to obtain a single mean value.

Example 1

Static Testing

Figure 7A:
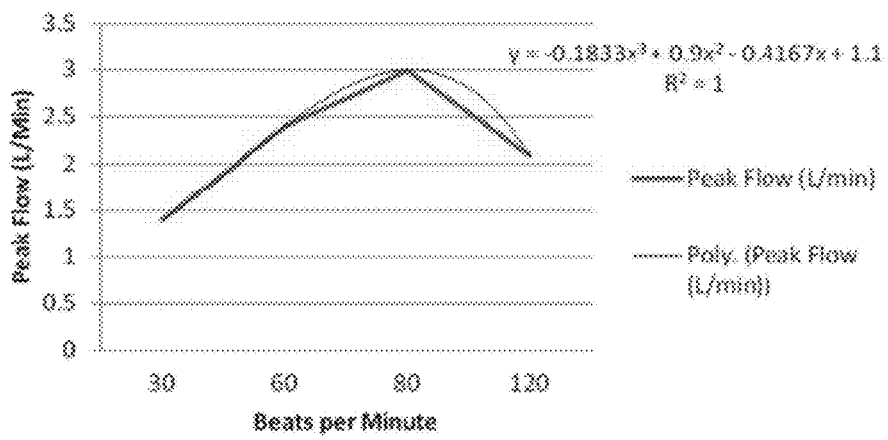
FIGS. 7A-7B are graphs showing the result of static testing demonstrating that operating an exemplary system made in accordance with the presently-disclosed subject matter at 80 beats per minute and an inflation and deflation time delay of 150-175 ms between the cuff chambers generated the largest device flows.
Figure 7B:
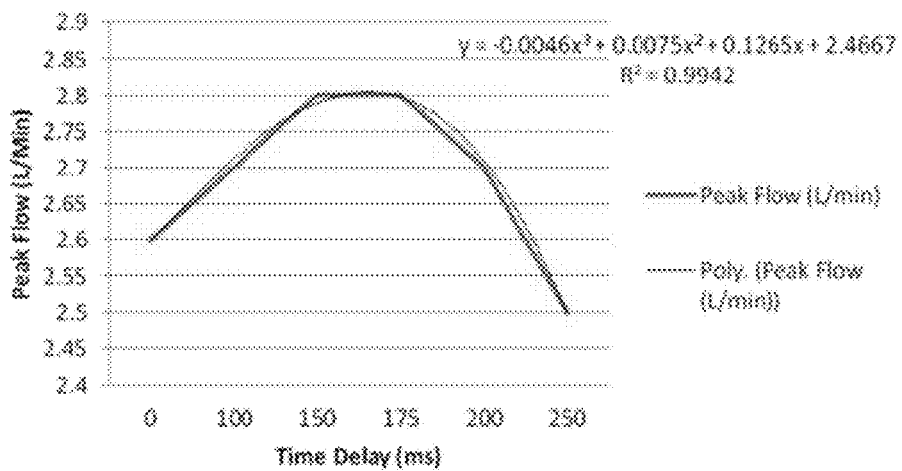

Static testing demonstrated that operating the peristaltic CPAD at 80 beats per minute and an inflation and deflation time delay of 150-175 ms between the cuff chambers generated the largest device flows (FIGS. 7A-7B). Further, cuff inflation times of 300 ms were required to provide optimal peristaltic action. Device generated flows increased with increases in cuff inflation volume.

Example 2

Dynamic Testing

Figure 8:
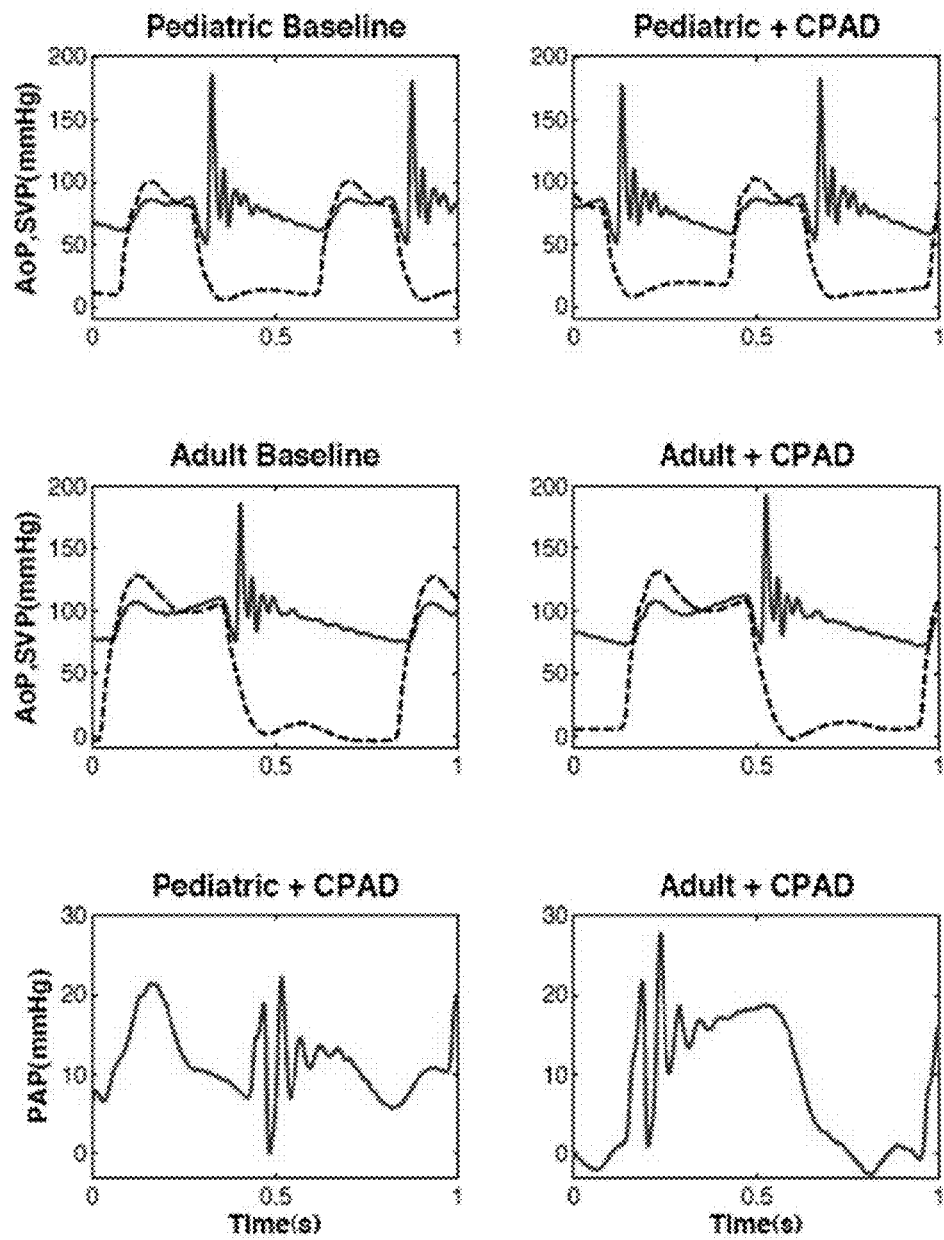
FIG. 8 includes a series of graphs showing that an exemplary system made in accordance with the presently-disclosed subject matter increased ventricular end diastolic pressures, augmented aortic systolic and diastolic pressures, and augmented pulmonary arterial pressure pulsatility.

Dynamic adult Fontan mock circulatory system experiments demonstrate that the peristaltic CPAD augmented the cavopulmonary pressure head by 6 mmHg and cardiac output by 10% in with a total device inflation volume of 42 mL (Table 1A). Peristaltic CPAD with a 28 mL inflation volume augments the pediatric cavopulmonary pressure head by up to 7 mmHg and cardiac output by up to 16.4% (Table 1B). The improvement in circulatory status provided by the peristaltic CPAD is similar to improvements observed with rotary cavopulmonary assist devices (Table 1C). However, in contrast to rotary cavopulmonary assist devices, the CPAD augmented pulmonary arterial pressures in both pediatric and adult Fontan circulations (FIG. 8). Further, CPAD support increased pulmonary arterial pressure, aortic systolic and diastolic pressures, and ventricular end-systolic and end-diastolic volumes. Importantly, only modest (6-7 mmHg) shift of cavopulmonary pressure head in the direction of the single ventricle leads to these significant improvements in hemodynamic parameters of the Fontan circulation. When the CPAD was operated in the SVC or IVC only, it augmented mean and peak pressures and some retrograde flows on the opposing vena cava. These retrograde flows and backpressure were minimized when the CPAD was placed on both the SVC and IVC, even with a significantly larger cuff inflation volume in the IVC. When the CPAD was stopped to simulate device failure, the cuffs deflated within 20 seconds and baseline Fontan flows were restored. A single chambered cuff (non-peristaltic) augmented pulmonary artery pressure pulsatility but did not augment the Fontan flow due to significant retrograde flow during device deflation.

TABLE 1(A)

| Case | CPAD SV (mL) | SV (mL) | CO (L/min) | CO % increase | PAP – VCP (mmHg) |
|---|---|---|---|---|---|
| Fontan baseline | — | 54.8 | 4.06 | — | −1 |
| Fantail + support | 21 | 57.7 | 4.27 | 5.2% | 4 |
| Fontan + support | 28 | 58.6 | 4.34 | 6.9% | 5 |
| Fontan + support | 42 | 60.3 | 4.46 | 9.9% | 6 |

TABLE 1(B)

| Case | CPAD SV (mL) | SV (mL) | CO (L/min) | CO % increase | PAP – VCP (mmHg) |
|---|---|---|---|---|---|
| Fontan baseline | — | 24.8 | 2.32 | — | −1 |
| Fontan + support | 21 | 26.9 | 2.56 | 10.3% | 3 |
| Fontan + support | 28 | 28.3 | 2.70 | 16.4% | 7 |

TABLE 1(C)

| Case | VIP speed (RPM) | SV (mL) | CO (L/min) | CO % increase | PAP – VCP (mmHg) |
|---|---|---|---|---|---|
| Fontan baseline | — | 20 | 2.2 | — | −1 |
| Fontan + VIP | 3000 | 20.9 | 2.3 | 4.5% | 3 |
| Fontan + VIP | 5000 | 21.8 | 2.4 | 9.1% | 4 |
| Fontan + VIP | 7000 | 24.1 | 2.65 | 20.4% | 8 |

Table 1. (A) Simulation of cavopulmonary support system flow for adult Fontan circulation without, and with CPAD support. (B) Simulation of cavopulmonary assist device flow for pediatric Fontan circulation without, and with CPAD support. (C) Simulation of cavopulmonary assist device flow for pediatric Fontan circulation without, and with rotary cavopulmonary assist device (VIP) support. CPAD support increases the Fontan circulation cavopulmonary pressure head (difference of pulmonary arterial and vena caval pressure), cardiac output, and aortic pressures. The performance of the CPAD is comparable to the VIP. SV: stroke volume; CO: cardiac output; CO % increase: percent increase from baseline Fontan cardiac output; AoP: aortic pressure; cavopulmonary pressure head=pulmonary artery pressure (PAP)—vena cava pressure (VCP); VIP: viscous impeller pump.

Discussion of Examples 1-2

Mechanical cavopulmonary assist within the total cavopulmonary connection (TCPC) presents unique anatomic and physiologic challenges, which are markedly dissimilar to any other mechanical circulatory support application. Flow must be augmented in a highly complex 3- or 4-axis geometry in which incoming and outgoing flows are perpendicular. The pump will need to provide support in a location where no ventricle will recover to assume function of the pump; thus, it is not a ventricular assist device. The ambient cavopulmonary pressures are low (10-15 mmHg) and the ideal pump should generate a substantial amount of flow while maintaining a low pressure head (5-10 mmHg) to avoid perfusion injury to the lung. It is important that the cavopulmonary pathways remain unobstructed during pump deployment, weaning, pump shut off or failure, and after the pump is withdrawn.

Implantation of microaxial pumps in the superior and/or inferior vena cavae have been proposed as a means of providing cavopulmonary support. Implantation of one microaxial pump in the superior or inferior vena cava alone would lead to undesirable back pressure in the opposing vena cava. Implantation of two microaxial pumps in the superior and inferior vena cavae have significant limitations: (1) need to implant two devices to satisfactorily augment the double inlet, double outlet flow pattern characteristic of the TCPC, increasing the complexity of implantation and explanation, and risk of failure; (2) obstructive to flow, which significantly limits the ability to wean support to no net contribution to Fontan flow, and may be catastrophic in the event of pump failure; (3) have an inherently high risk of inlet suction due to high rotational speed; (4) any imbalance in flows between the pumps will lead to undesirable back pressure; and (5) have a high degree of complexity and very low manufacturing tolerances, which may increase risk of mechanical failure. To avoid these limitations, modification of the existing Fontan junction to a Y-shaped three-way junction has been proposed. While this approach enables Fontan support using a single microaxial pump, it would require an additional major surgical procedure with cardiopulmonary bypass to reconstruct the Fontan cavopulmonary junction. Further, implantation of a microaxial pump in a 3-way junction (+/−barrier to recirculation) would have obstructive potential, which will complicate the ability to wean cavopulmonary support and may be catastrophic in the case of pump failure. A percutaneously implanted, expanding, bi-conical viscous impeller pump (VIP) that allows for a single impeller to stabilize and augment cavopulmonary flow in 4 axes has been proposed. The VIP requires no reconstruction of the existing cavopulmonary junction and is not obstructive during implantation or pump failure. However, the VIP may not be implantable if there is a significant vena caval offset. Further, all rotary blood pumps have a thrombosis risk as they come in contact with blood, requiring oral anticoagulation therapy. Catheter-based microaxial pumps and VIP, while minimally invasive, can only be used for short-term support (2-4 weeks) due to the risk of septicemia. Further, percutaneous access would restrict the mobility of the patients implanted with these devices. Rotary pumps also diminish pulmonary arterial pressure pulsatility. This diminished pressure pulsatility has been associated with reduced pulmonary endothelial cell nitric oxide production, size, and morphology and is hypothesized to play a role in pulmonary hypertension and arteriovenous malformations in the lung. Thus, a long-term CSD that can overcome these limitations can have a significant clinical impact.

The above-described study demonstrated that the peristaltic CPAD may augment cavopulmonary flow, and restore cardiac output, ventricular pressures and volumes, and aortic pressures with only a modest rise in cavopulmonary pressure head (6-7 mmHg). These hemodynamic benefits were observed with the CPAD operating at nominal stroke volumes in both simulated adult and pediatric Fontan patients (Table 1). These benefits can be achieved by placing the CPAD cuffs on their IVC and SVC grafts/vena cavae. Alternately, the CPAD may be integrated with the implantable SVC and IVC grafts. The peristaltic CPAD requires a more invasive surgery for implantation compared to percutaneous pumps. However, in contrast to percutaneous devices that are only suitable for short-term implantation, the peristaltic device allows for long-term support of failing Fontan patients. Further, it can be operated by a portable pneumatic driver that weighs approximately 2 kg, allowing for significant patient mobility and quality of life. The CPAD does not require anticoagulation therapy as it is non-blood contacting. The risk of infection with CPAD would be lower compared to percutaneous devices and should be comparable to the risk of driveline infections associated with current ventricular assist device patients. Venting of the driveline during CPAD failure restores baseline Fontan hemodynamics within 20 seconds, demonstrating failure tolerance of this design. CPAD also augments the pulmonary arterial pressure pulsatility to normal values, which may normalize pulmonary arterial endothelial cell function.

Animal models of univentricular Fontan circulation that accurately replicate Fontan hemodynamics do not exist, making it a challenge to test the circulatory response to cavopulmonary assist prior to clinical application. Mock circulation of the Fontan circulation is representative of clinical observations from a hemodynamic viewpoint. The biventricular mock circulation model, modified to simulate univentricular Fontan circulation in the foregoing study, has been validated and used in the development and testing of several blood pumps, and does provide a controlled environment to test the effects of CPAD support and potential failure modes, which is valuable in device development and is not possible in vivo. The ventricular contractility and heart rate were kept constant to reduce experimental variability. Physiologically, heart rate and the contractility will increase with increasing preload in accordance with the Frank-Starling mechanism. By extension, it is reasonable to assume that the increase in cardiac output with CPAD support may be greater clinically due to Frank-Starling response. The mock circulation system has mechanical valves, which may create large aortic valve pressure gradients and ringing during valve closure. The length of tubing in the mock circulation may cause added inertial effects. However, the inertial effects represent less than 2% of the total power and an inertance mismatch would not affect the results significantly. The prototype device required each CPAD chamber to be inflated and deflated with a separate driveline to optimize the time delay. However, with a single driveline and a 0.08" opening between the proximal and distal CPAD chambers naturally resulted in a 150 ms delay. In all, the study demonstrated the efficacy of an adult- and pediatric-scale peristalitic Fontan cavopulmonary assist device with minimal risk of thrombosis.

Throughout this document, various references are mentioned. All such references are incorporated herein by reference, including the references set forth in the following list:

REFERENCES

1. Rodefeld M D, Frankel S H, and Giridharan G A. Cavopulmonary Assist: (Em)powering the Univentricular Fontan Circulation. Seminars in Thoracic and Cardiovascular Surgery: Pediatric Cardiac Surgery Annual, 2011; 14(1):45-54.
2. Anderson P A, Sleeper L A, Mahony L, Colan S D, Atz A M, Breitbart R E, et al. Contemporary outcomes after the Fontan procedure: a Pediatric Heart Network multicenter study. J Am Coll Cardiol. 2008; 52:85-98.
3. Hsu D T, Pearson G D. Heart Failure in Children. Part II: Diagnosis, Treatment, and Future Directions. Circ Heart Fail 2009; 2:490-8.
4. Goldberg D J, French B, McBride M G, Marino B S, Mirarchi N, Hanna B D, Wernovsky G, Paridon S M, Rychik J. Impact of oral sildenafil on exercise performance in children and young adults after the fontan operation: a randomized, double-blind, placebo-controlled, crossover trial. Circulation. 2011; 123:1185-93.
5. Kanter K R, Haggerty C M, Restrepo M, de Zelicourt D A, Rossignac J, Parks W J, Yoganathan A P. Preliminary clinical experience with a bifurcated Y-graft Fontan procedure—a feasibility study. J Thorac Cardiovasc Surg. 2012; 144:383-9.
6. Mackling T, Shah T, Dimas V, Guleserian K, Sharma M, Forbess J et al. Management of single-ventricle patients with Berlin EXCOR ventricular assist device: Single-center experience. Artif Organs 2012; 36(6):555-9.
7. Vanderpluym C J, Rebeyka I M, Ross D B, Holger B. The use of ventricular assist devices in pediatric patients with univentricular hearts. J Thorac Cardiovasc Surg 2011; 141: 588-90.
8. Newcomb A E, Negri J C, Brizard C P, and d'Udekem Y. Successful left ventricular assist device bridge to transplantation after failure of Fontan revision. J Heart Lung Transplant 2006; 25:365-7.
9. Rodefeld M D, Boyd J H, LaLone B J, Bezrucko A J, Potter A W, Brown J W. Cavopulmonary assist: circulatory support for the univentricular Fontan circulation. Ann Thorac Surg 2003; 76:1911-6.
10. Rodefeld M D, Coats B, Fisher T, Giridharan G A, Chen J, Brown J W, Frankel S H. Cavopulmonary assist for the univentricular Fontan circulation: von Karman viscous impeller pump. J Thorac Cardiovasc Surg 2010; 140:529-36.
11. Giridharan G A, Koenig S C, Kennington J, Sobieski M A, Chen J, Frankel S H, and Rodefeld M D. Performance evaluation of a pediatric viscous impeller pump for Fontan cavopulmonary assist. Journal of Thoracic and Cardiovascular Surgery 2012; DOI: 10.1007/s13239-012-0096-4. (In press)
12. Kennington J R, Frankel S H, Chen J, Koenig S C, Sobieski M A, Giridharan G A, and Rodefeld M D. Design Optimization and Performance Studies of an Adult Scale Viscous Impeller Pump for Powered Fontan in an Idealized Total Cavopulmonary Connection. Cardiovascular Engineering and Technology 2011; 2(4):237-243.
13. Lacour-Gayet F G, Lanning C J, Stoica S, Wang R, Rech B A, Goldberg S, Shandas R. An artificial right ventricle for failing fontan: in vitro and computational study. Ann Thorac Surg. 2009; 88(1):170-6.
14. Shiraishi Y, Sugai T K, Tanaka A, Yoshizawa M, Yambe T, Yamada A, Omran M H, Shiga T, Kitano T, Kamiya K, Mochizuki S, Miura H, Homma D, Yamagishi M. Structural design of a newly developed pediatric circulatory assist device for Fontan circulation by using shape memory alloy fiber. Conf Proc IEEE Eng Med Biol Soc. 8353-5, 2011.
15. Drew G A, Koenig S C. Biomedical patient monitoring, data acquisition, and playback with LabVIEW®. In: Olansen J B, Rosow E, editors. Virtual bio-instrumentation: biomedical, clinical, and healthcare applications in LabVIEW®. Upper Saddle River, N.J.: Prentice Hall; 2002; 180-6.
16. Koenig S C, Woolard C, Drew G D, Unger L, Gillars K J, Ewert D L, Gray L A, Pantalos G M. Integrated data acquisition system for medical device testing and physiology research in compliance with Good Laboratory Practices. Biomed Instrum Technol 2004; 38:229-40.
17. Schroeder M J, Perrault B, Ewert D L, Koenig S C. HEART: an automated beat-to-beat cardiovascular analysis package using Matlab. Comput Biol Med 2004; 34:371-88.
18. Giridharan G A, Pantalos G M, Koenig S C, Mitchell M, Austin E, Gartner M. A computer model of pediatric circulatory systems for testing pediatric assist devices. ASAIO J 2007; 53:74-81.
19. Pantalos G M, Koenig S C, Gillars K J, Giridharan G A, and Ewert D L. Characterization of an adult mock circulation for testing cardiac support devices. *ASAIO Journal*, 2004; 50:37-46.
20. Giridharan G A, G M Pantalos, S C Koenig, K J Gillars, and M Skliar. Physiologic control of rotary blood pumps: An in vitro study. *ASAIO Journal*, 2004; 50:403-409.
21. Litwak K N, Koenig S C, Giridharan G A, Gillars K J, and Pantalos G M. Ascending aorta outflow graft location and pulsatile ventricular assist provide optimal hemodynamic support in an adult mock circulation. *Artificial Organs*, 2005; 29:629-635.
22. Kaebnick B W, Giridharan G A, and Koenig S C. Quantification of pulsatility as a function of vascular input impedance: An in-vitro study. *ASAIO Journal*, 53(2):115-121, 2007.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A system for providing cavopulmonary support to a subject, comprising:
   a first inflatable extravascular cuff configured to be placed around a superior vena cava in the subject;
   a second inflatable extravascular cuff configured to be placed around an inferior vena cava in a subject;
   a pump operably connected to the first inflatable extravascular cuff and the second inflatable extravascular cuff; and
   a controller in communication with the pump, the controller for receiving one or more user-defined parameters and for independently controlling the inflation and deflation of the first inflatable extravascular cuff and the second inflatable extravascular cuff in response to the user-defined parameters,
   wherein the user-defined parameters are directed to a selected timing for inflating and deflating the first inflatable extravascular cuff, the second inflatable extravascular cuff, or both;
   and wherein the first inflatable extravascular cuff and the second inflatable extravascular cuff are configured to inflate and deflate peristaltically in response to the user-defined parameters to provide cavopulmonary support.

2. The system of claim 1, wherein the first inflatable extravascular cuff and the second inflatable extravascular cuff each include a proximal chamber and a distal chamber, each proximal chamber and each distal chamber separated from one another such that each proximal chamber and each distal chamber are configured to be inflated and deflated independently.

3. The system of claim 2, wherein the user-defined parameters include a time delay between the inflation or the deflation of the proximal chamber and the distal chamber of the first inflatable extravascular cuff and the second inflatable extravascular cuff.

4. The system of claim 1, wherein the first extravascular cuff and the second extravascular cuff can each be characterized as including a lower end, a central portion, and an upper end, and wherein each vascular cuff includes a hollow chamber and a plurality of internal barriers positioned in the hollow chamber for peristaltically directing fluid flow through each hollow chamber.

5. The system of claim 4, wherein the first inflatable extravascular cuff and the second inflatable extravascular cuff each further include a fluid supply line positioned at the lower end of each inflatable extravascular cuff such that each inflatable extravascular cuff inflates and deflates peristaltically from the lower end to the upper end of each inflatable extravascular cuff.

6. The system of claim 4, wherein the first inflatable extravascular cuff and the second inflatable extravascular cuff each further include a fluid supply line positioned in the central portion of each inflatable vascular cuff such that each extravascular cuff inflates and deflates peristaltically from the central portion to the lower end and to the upper end of each inflatable extravascular cuff.

7. The system of claim 1, wherein both the first inflatable extravascular cuff and the second inflatable extravascular cuff have a length sufficient to allow each inflatable extravascular cuff to be spirally wound around the superior vena cava or the inferior vena cava.

8. The system of claim 1, further comprising:
   a third inflatable extravascular cuff configured to be placed around the left pulmonary artery; and
   a fourth inflatable extravascular cuff configured to be placed around the right pulmonary artery,
   wherein both the third inflatable extravascular cuff and the fourth inflatable extravascular cuff are operably connected to the pump such that the controller further independently controls the inflation and deflation of the third inflatable extravascular cuff and the fourth inflatable extravascular cuff,
   and wherein the third inflatable extravascular cuff and the fourth inflatable extravascular cuff are also configured to inflate and deflate peristaltically in response to the user-defined parameters to provide cavopulmonary support.

9. The system of claim 1, wherein the user-defined parameters cause the first extravascular cuff and the second extravascular cuff to inflate and deflate to alter one or more conditions selected from the group consisting of cavopulmonary pressure head, cardiac output, pulmonary artery pressure, aortic systolic pressure, aortic diastolic pressure, left ventricular end-systolic volume, left ventricular end-diastolic volume, and combinations thereof.

10. The system of claim 1, further comprising one or more sensors operably connected to the controller, the sensors for measuring the pressure and flow of blood in the subject such that the controller adjusts the inflation and deflation of the first inflatable extravascular cuff and the second inflatable extravascular cuff in response to feedback from the one or more sensors.

11. The system of claim 1, further comprising an artificial cavopulmonary junction including four collapsible cannulas in fluid communication with each other, each of the collapsible cannulas configured to be anastomosed to a vena cava or a pulmonary artery.

12. A system for providing cavopulmonary support to a subject, comprising:
   a first inflatable extravascular cuff including a proximal air chamber and a distal air chamber, the first inflatable extravascular cuff configured to be placed around a superior vena cava in the subject;
   a second inflatable extravascular cuff including a proximal air chamber and a distal air chamber, the second inflatable extravascular cuff configured to be placed around an inferior vena cava in a subject;
   a pump operably connected to the first extravascular cuff and the second extravascular cuff; and
   a controller in communication with the pump, the controller for receiving one or more user-defined parameters and for independently controlling the inflation and deflation of the proximal air chamber and the distal air chamber in both the first inflatable extravascular cuff and the second inflatable extravascular cuff in response to the user-defined parameters,
   wherein the user-defined parameters are directed to a selected timing for inflating and deflating the proximal air chamber and the distal air chamber in both the first extravascular cuff and the second extravascular cuff;
   and wherein the first inflatable extravascular cuff and the second inflatable extravascular cuff are configured to inflate and deflate peristaltically in response to the user-defined parameters to provide cavopulmonary support.

13. The system of claim 12, wherein the user-defined parameters include a time delay between the inflation or the deflation of the proximal chamber and the distal chamber of each inflatable extravascular cuff.

14. A method for providing cavopulmonary support to a subject, comprising:
  providing a system including a first inflatable extravascular cuff configured to be placed around a superior vena cava in the subject and a second inflatable extravascular cuff configured to be placed around an inferior vena cava in a subject, both the first inflatable extravascular cuff and the second inflatable extravascular cuff being configured to inflate and deflate peristaltically in response to one or more user-defined parameters; and
  selectively inflating and deflating the first inflatable extravascular cuff, the second inflatable extravascular cuff, or both to provide cavopulmonary support.

15. The method of claim 14, wherein the system further comprises a controller for receiving the one or more user-defined parameters and for independently controlling the peristaltic inflation and deflation of the first inflatable extravascular cuff and the second inflatable extravascular cuff in response to the user-defined parameters, and
  wherein the step of selectively inflating or deflating the first inflatable extravascular cuff, the second inflatable extravascular cuff, or both comprises inputting the one or more user-defined parameters into the controller.

16. The method of claim 15, wherein the user-defined parameters are directed to a selected timing for inflating and deflating the first inflatable extravascular cuff, the second inflatable extravascular cuff, or both to provide cavopulmonary support.

17. The method of claim 15, wherein the user-defined parameters cause the first inflatable extravascular cuff and the second inflatable extravascular cuff to inflate and deflate to alter one or more conditions selected from the group consisting of cavopulmonary pressure head, cardiac output, pulmonary artery pressure, aortic systolic pressure, aortic diastolic pressure, left ventricular end-systolic volume, left ventricular end-diastolic volume, and combinations thereof.

18. The method of claim 14, wherein the first inflatable extravascular cuff and the second inflatable extravascular cuff each include a proximal chamber and a distal chamber, each proximal chamber and each distal chamber separated from one another such that each proximal chamber and each distal chamber are configured to be inflated and deflated independently from one another, and
  wherein the step of inflating or deflating the first inflatable extravascular cuff, the second inflatable extravascular cuff, or both comprises selectively inflating the proximal chamber, the distal chamber, or both of each inflatable extravascular cuff.

19. The method of claim 18, wherein the step of inflating or deflating the first extravascular cuff, the second extravascular cuff, or both comprises inflating the distal chamber of each inflatable extravascular cuff and subsequently inflating the proximal chamber of each inflatable extravascular cuff.

20. The method of claim 19, further comprising the step of deflating the distal chamber of each inflatable extravascular cuff and subsequently deflating the proximal chamber of each inflatable extravascular cuff.

* * * * *

UNITED STATES PATENT AND TRADEMARK OFFICE
CERTIFICATE OF CORRECTION

PATENT NO.        : 9,227,002 B1                     Page 1 of 1
APPLICATION NO.   : 14/304614
DATED             : January 5, 2016
INVENTOR(S)       : Guruprasad A. Giridharan et al.

It is certified that error appears in the above-identified patent and that said Letters Patent is hereby corrected as shown below:

In the Claims,

Claim 11, col. 20, line 33, change "cavopulomonary" to "cavopulmonary"

Signed and Sealed this
Seventeenth Day of May, 2016

Michelle K. Lee
*Director of the United States Patent and Trademark Office*